United States Patent [19]

Nagata et al.

[11] Patent Number: 5,504,581
[45] Date of Patent: Apr. 2, 1996

[54] METHOD AND APPARATUS FOR MEASURING BIREFRINGENCE

[75] Inventors: Shinichi Nagata, Osaka; Kiyokazu Sakai, Hyogo; Osamu Tomita, Osaka; Kyoji Imagawa, Hyogo, all of Japan

[73] Assignee: Kanzaki Paper Manufacturing Company, Ltd., Japan

[21] Appl. No.: 23,384

[22] Filed: Feb. 26, 1993

[30] Foreign Application Priority Data

| Feb. 29, 1992 | [JP] | Japan | 4-079067 |
| Feb. 29, 1992 | [JP] | Japan | 4-079068 |
| Feb. 29, 1992 | [JP] | Japan | 4-079069 |

[51] Int. Cl.$^6$ ................................. G01J 4/00
[52] U.S. Cl. .............................. 356/364; 356/365
[58] Field of Search ........................ 356/364, 365

[56] References Cited

U.S. PATENT DOCUMENTS 3,902,805 9/1975 Redner ........................ 356/33

*Primary Examiner*—William Mintel
*Assistant Examiner*—Roy Potter
*Attorney, Agent, or Firm*—Klima & Hopkins

[57] ABSTRACT

A phase plate is superposed on a sample, and this phase plate is so adjusted that the phase difference of the total retardation of the sample and the phase plate is integral times $2\pi$ with respect to a measuring beam of a first wavelength, so that retardation can be correctly measured even if an order is increased. In this state, a measuring beam of a second wavelength which is approximate to the first wavelength is employed and two polarizing plates maintaining polarizing directions in parallel nicol relation are singularly rotated with respect to the sample which is arranged therebetween. The ratio Im/Io between maximum value Io and minimum value Im of currently transmitted light intensity is applied to a previously prepared relation between the order n of retardation and this ratio Im/Io to derive the order of retardation of the sample, to thereafter obtain correct retardation.

15 Claims, 7 Drawing Sheets

FIG.1A
FIG. 1B
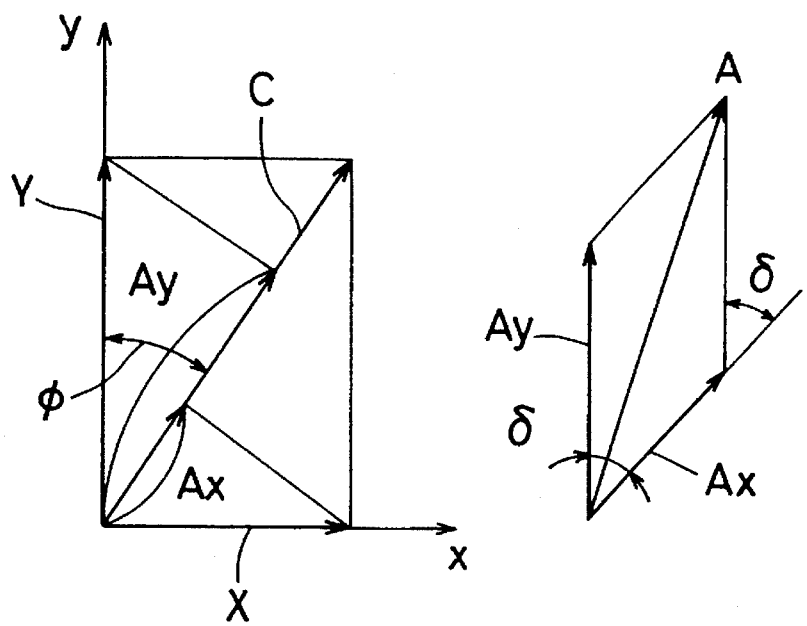
FIG. 2
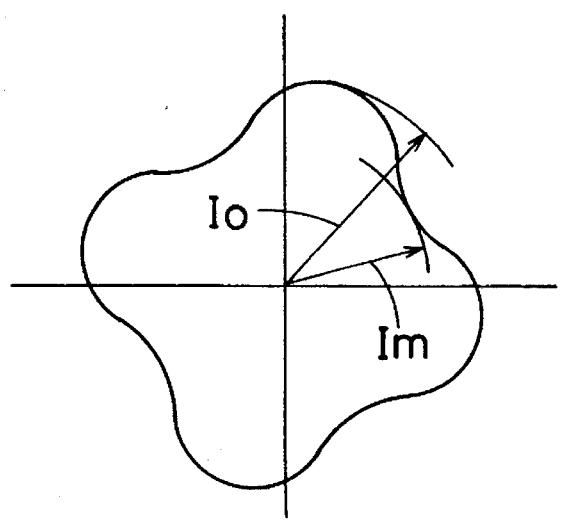

TO CPU

METHOD AND APPARATUS FOR MEASURING BIREFRINGENCE

BACKGROUND OF THE INVENTION

1. Field of the Invention

The present invention relates to a method and an apparatus for measuring retardation of a birefringent material.

2. Description of the Background Art

A drawn plastic sheet generally exhibits birefringence. As to the same material, it is possible to determine the degree of drawing of a sheet on the basis of the degree of birefringence if the sheet has a constant thickness, while it is possible to determine the thickness if the sheet has a constant degree of drawing. Such a birefringent sheet is applied to a liquid crystal display, for example, and it is necessary to measure birefringence also in this case. In addition to this, birefringence of such a sheet material is measured for various purposes. Further, it may be necessary to measure refractive indices along three axial directions of the sheet material.

Birefringence is expressed in refractive indices of ordinary and extraordinary rays, and the difference therebetween appears as phase difference between the ordinary and extraordinary rays transmitted through a sample. This phase difference is called retardation, which is defined by the product of the difference between the two refractive indices and the thickness of the material. Birefringence of the sheet sample is recognized by measurement of such retardation.

In a conventional method of measuring retardation, a sample is placed between two polarizing plates which are arranged in a parallel or crossed nicol manner, so that either of the polarized plates and the sample is rotated. Changes of light transmitted through the polarizing plates and the sample are recorded to obtain retardation from the results by calculation. Such retardation is observed as phase difference between ordinary and extraordinary rays, which are introduced into the sample in the same phase, outgoing from the sample, and this phase difference is generally expressed as $(2n\pi+\delta)$, where n represents a natural number of $0, 1, 2 \ldots$, which is called an order. This order n is increased as the thickness of the sample is increased. The change width of transmitted light intensity which is obtained by rotating either of the polarizing plates and the sample is varied with the value $\delta$. Only this value $\delta$ is directly obtained through the measurement, and there is no method of directly obtaining the order n.

In general, therefore, two beams having different wavelengths are employed to obtain phase difference $\delta$ corresponding to retardation for each beam. Then the order n is successively changed as $1, 2, 3 \ldots$ to calculate back retardations corresponding to the respective orders, thereby regarding such an order n as correct that retardations calculated as to the two beams of different wavelengths most coincide with each other. According to this method, however, difference $\Delta$ of the phase difference by the two beams of the different wavelengths can be obtained only up to $2\pi$, and it is impossible to decide an integer m when the difference is $2\pi m+\Delta'$, where m represents $1, 2, 3 \ldots$, and $\Delta'$ represents 0 to $2\pi$. In practice, therefore, application of this method is limited to an order n of retardation of about 20, and hence it is impossible to measure a thick sample having a large retardation. Further, there is an apprehension for erroneous decision of the order on the assumption that m=0 even if the order n of retardation is in excess of 20 and the aforementioned integer m is $1, 2, \ldots$ When the retardation is around $n\lambda/2$ ($\lambda$: measuring wavelength), the phase difference is around $n\pi$ to deteriorate resolution, and it is difficult to correctly decide the retardation value.

SUMMARY OF THE INVENTION

A first object of the present invention is to enable correct measurement of retardation even if an order of the retardation is increased.

A second object of the present invention is to enable correct measurement of retardation even if an order is increased, as well as to enable measurement of the retardation in high resolution even if phase difference is around $\pi$.

A third object of the present invention is to enable correct measurement of retardation even if an order is increased, as well as to automatically improve resolution when phase difference is around $\pi$.

A fourth object of the present invention is to enable correct measurement of retardation even if an order is increased, as well as to enable measurement of refractive indices in three axial directions of a sample.

A fifth object of the present invention is to provide a composite measuring apparatus which can correctly measure retardation of a high order on its own in high resolution regardless of phase difference while enabling measurement of refractive indices in three axial directions.

In order to enable correct measurement of retardation even if an order is increased, a phase plate is so superposed on a sample that the phase difference of the total retardation of the sample and the phase plate is integral times $2\pi$ with respect to a beam of one wavelength, while another beam having another wavelength which is approximate to the aforementioned wavelength is employed in this state and two polarizing plates (a polarizer provided on a light source side and an analyzer provided on a detector side) maintaining polarizing directions in a constant relation are relatively rotated with respect to the sample which is held therebetween so that the ratio between a maximum value Io and a minimum value Im of the currently transmitted light intensity is applied to a previously prepared relation between the order of retardation and the ratio to derive the order of retardation of the sample, thereby obtaining correct retardation. In the present invention, the ratio between Io and Im involves both of Im/Io and (Io–Im)/Io.

A plate of known retardation such as a quarter-wavelength plate, for example, is provided to be insertable on and removable from an optical axis of a refractometer so that retardation can be measured in high resolution even if phase difference between ordinary and extraordinary rays is around $n\pi$. In order to automatically improve resolution when phase difference is around $n\pi$, means for detecting that the phase difference is around $n\pi$ is provided so that a plate of known retardation such as a quarter-wavelength plate, for example, is automatically inserted on the optical axis of the refractometer on the basis of the result detected by the means. To this end, a measuring apparatus of a system of placing a sample between two polarizing plates maintaining polarizing directions in a constant relation, relatively rotating the two polarizing plates with respect to the sample and deriving retardation of the sample from maximum and minimum values of intensity of light transmitted through the two polarizing plates and the sample is provided with detection means for detecting whether or not the ratio or difference between maximum and minimum values of the transmitted light is within a predetermined reference range, means for inserting and removing a plate of known retardation such as a quarter-wavelength plate for superposing the plate of known retardation on the sample between the two polarizing plates depending on whether or not the ratio or difference between the maximum and minimum values of the transmitted light intensity is within the predetermined reference range, means for detecting an azimuth of the sample, i.e., the azimuth of its optical principal axis providing the maximum value of the transmitted light intensity, means for matching an azimuth of an optical principal axis of the plate of known retardation with that of the sample, and a data processor for obtaining retardation in a state removing the plate of known retardation from a measuring optical path when the detection means detects that the ratio or difference between the maximum and minimum values of the transmitted light intensity is within the reference range while matching the azimuth of the optical principal axis of the plate of known retardation with that of the sample and superposing the plate of known retardation on the sample and again detecting maximum and minimum values of the transmitted light intensity for obtaining retardation when the ratio or difference between the maximum and minimum values of the transmitted light intensity is not within the reference range.

In order to enable measurement of refractive indices in three axial directions of the sample, the sample is rendered rotatable in its plane as well as inclinable about a straight line along its surface, thereby measuring the refractive indices while rotating and inclining the sample by constant angles.

A method of measuring retardation is now described. Referring to FIG. 1A, optical principal axes x and y of orthogonal two directions are parallel to a sheet surface of a sample, while two polarizing plates which are arranged in a parallel nicol manner to hold the sample are polarized in a direction C. A measuring beam enters the sample through the upper polarizing plate. The arrow C denotes an amplitude vector of the beam which enters the sample through the upper polarizing plate. The beam expressed by the vector C is separated into a y direction component Y (called an ordinary ray) and an x direction component X (called an extraordinary ray), to progress in the sample. Components Ax and Ay of the amplitude vectors X and Y in the vector C direction are transmitted through the polarizing plate which is provided under the sample. At this time, phase difference $\delta$ is caused between the light components of the amplitude vectors Ax and Ay which are transmitted through the sample. Assuming that A represents the amplitude of the beam, which is a composition of the two beams of the amplitudes Ax and Ay of the same spatial vector direction having the phase difference $\delta$, transmitted through the polarizing plate provided under the sample and I represents the intensity thereof, $$I = A^2 \quad (1)$$
$$= Ax^2 + Ay^2 + 2AxAy\cos\delta$$
$$\delta = 2\pi R/\lambda$$

where R represents retardation and $\lambda$ represents the wavelength of the measuring beam in the air.

Assuming that Io represents intensity of the beam entering the sample and $\phi$ represents an azimuth angle of the amplitude vector, $$Ax = X \sin\phi = C \sin^2\phi$$
$$Ay = Y \cos\phi = C \cos^2\phi$$

Substitution of these in the equation (1) with C=Io gives:

$$I = Io\ [\sin^4\phi + \cos^4\phi + 2\sin^2\cos^2\cos\delta]$$

Rearrangement of this equation gives:

$$I/Io = 1 - \sin^2 2\phi(1-\cos\delta)/2 \quad (2)$$

The equation (2) is maximized as I=Io when $\sin 2\phi=0$. When $\sin 2\phi=1$, on the other hand, the equation (2) is minimized as follows:

$$I/Io = (1+\cos\delta)/2$$

When the sample is relatively rotated between the two polarizing plates which are arranged in a parallel nicol manner to measure a transmitted light intensity pattern as shown in FIG. 2, it is possible to obtain the cosine of the phase difference $\delta$ as follows:

$$\cos = 2Im/Io - 1 \quad (3)$$

where Io represents the maximum transmitted light intensity and Im represents the minimum transmitted light intensity.

A method of deriving an order n is now described. From the equation (3), the minimum intensity is expressed as follows:

$$Im = Io\ (1+\cos\delta)/2$$

Introduction of the order n in this gives:

$$Im = Io\ (1+\cos(2n\pi+\delta))/2 \quad (4)$$

The value Im is changed between 0 and Io. FIG. 3 illustrates a sine waveform A showing changes of Im with retardation R shown on the axis of abscissa. The order n is increased by 1 every period of the waveform, as expressed in numerical values in FIG. 3. Assuming that $\lambda 1$ represents the wavelength of the measuring beam in the air having the waveform A, FIG. 3 also shows a sine waveform B of another measuring beam having a wavelength $\lambda 2$ in the air, which is slightly different from the wavelength $\lambda 1$. The waveforms A and B are slightly different in period from each other. A phase plate is superposed to move a position of Im to Im=Io in FIG. 3 which is a position of zero apparent phase difference based on the retardation with respect to the beam of the wavelength $\lambda 1$. Then Im is obtained with respect to the beam having the slightly different wavelength $\lambda 2$. This means that Im is obtained on the basis of the beam having the wavelength $\lambda 2$ when the waveform A in FIG. 3 is maximized, i.e., values of a, b, c, . . . are obtained. Connection of the Im values at the a, b, c, . . . on the waveform B gives a curve C, which is monotonously reduced as the order n is increased. This curve is zeroed on an order at which the waveforms A and B are overlapped in opposite phases, and thereafter monotonously increased.

Since an actual value of Im is varied with measuring conditions such as intensity of a light source, Im is preferably replaced by Im/Io or (Io−Im)/Io in practice.

The value of Im/Io is a function of the order n while an order zeroing Im/Io depends on the wavelengths of the two measuring beams, whereby it is possible to derive the order n from an actual value of Im/Io (or (Io−Im)/Io) by previously obtaining the relation between Im/Io (or (Io−Im)/Io) and the order n.

The order n may be derived in the following manner:

It is assumed that C1 represents $\cos\delta$ obtained when the phase plate is so superposed that apparent phase difference based on retardation is 0 with respect to the beam of the wavelength $\lambda 1$. In place of the measuring beam of the wavelength $\lambda 2$, $\cos\delta$ is obtained from the ratio Im/Io between the maximum value Io and minimum value Im of the pattern shown in FIG. 2 which is obtained by rotating the polarizing plates and measuring transmitted light intensity, and regarded as C2. When C2 and C1 are substituted in the following relational expression obtained from FIG. 3, a possible order n (even number) is derived:

$$C2 = C1 \cdot \sin[\pi/2 - (n/2)(\lambda 2 - \lambda 1) 2\pi/\lambda 2] \quad (5)$$

Alternatively, a graph showing the relation between the order n and Im/Io may be previously obtained using the measuring beams of the wavelengths $\lambda 1$ and $\lambda 2$ for applying the ratio Im/Io with the measuring beam of the wavelength $\lambda 2$ to the graph, thereby obtaining the order n on this graph.

A plurality of values may be obtained as to the possible order while successively changing the measuring wavelengths, to decide a single value of n from the values by a majority operation, for example.

Upon decision of the order n, the retardation can be obtained as follows, if a retardation increment r of the phase plate which is adapted to zero the apparent phase difference based on the retardation with respect to the beam of the wavelength $\lambda 1$ is known:

$$n\lambda 1 = r$$

If the retardation increment r is unknown, on the other hand, the phase plate is removed from the measuring optical path and the polarizing plates are relatively singularly rotated with respect to the sample to measure transmitted light with the measuring beam of the wavelength $\lambda 1$, whereby the retardation of the sample is obtained in a range of 0 to $2\pi$ and hence this retardation can be obtained using the as-decided order n as follows:

$$(n-1)\lambda 1 + R$$

Alternatively, a matrix showing correspondence between possible orders and retardations may be prepared every measuring wavelength to employ an order providing coincidence of retardation between respective measuring wavelengths as a true order as well as the current retardation.

The relation between Im/Io and the order n is as follows: It is assumed that $\lambda 1$ and $\lambda 2$ represent wavelengths of two measuring beams and v1 and v2 represent refractive indices of two optical principal axes of a sample. While such refractive indices have wavelength dependency, changes of the refractive indices at the wavelengths are negligible since the wavelengths $\lambda 1$ and $\lambda 2$ are approximate to each other. Assuming that measurement is made with the beam of the wavelength $\lambda 1$ and S represents such a thickness, being gradually increased from 0, of the sample that the pattern shown in FIG. 2 first forms a circle, $$\begin{aligned} R &= S(v1 - v2) \\ &= \lambda 1 \end{aligned} \quad (6)$$

At this time, phase difference $\delta$ in measurement with the beam of the wavelength $\lambda 2$ is as follows:

$$\begin{aligned} \delta &= 2\pi S(v1 - v2)/\lambda 2 \\ &= 2\pi + e \end{aligned}$$

When the thickness of the sample is integral (n) times S, phase difference based on the retardation with respect to the beam of the wavelength $\lambda 1$ is apparently 0 and the order is n. At this time, phase difference based on the retardation with respect to the beam of the wavelength $\lambda 2$ is as follows:

$$n\delta = 2 \; n\delta + ne$$

while apparent phase difference is ne. This ne reaches $2\pi$ when the curve C shown in FIG. 3 draws one period. Assuming that no represents the current n, $$\begin{aligned} 2\pi n_o S(v1 - v2)/\lambda 2 &= 2n_o \pi + n_o e \\ &= 2\pi(n_o + 1) \end{aligned}$$

Application of the equation (6) to this gives:

$$n_o \lambda 1/\lambda 2 = n_o + 1$$

Hence, $$n_o = \lambda 2/(\lambda 1 - \lambda 2) \quad (7)$$

and $n_o$ is decided only by the wavelength. When $\lambda 1$ and $\lambda 2$ are approximate to each other, no gives a large order and the order n can be decided from an actually measured value of Im/Io even if the order is large.

As understood from FIG. 3, it is difficult to precisely obtain $\delta$ (hence the retardation R) when cos is $\pm 1$, i.e., the phase difference $\delta$ is around integral times $\pi$, since the rate of change of cos $\delta$ with respect to change of $\delta$, i.e., the rate of change of Im is small. When cos $\delta$ is around 0, on the other hand, it is possible to precisely decide $\delta$ with excellent measuring sensitivity since $\delta$ and Im are changed in a proportional manner. When cos $\delta$ is around $\pm 1$, therefore, a sheet of known retardation, preferably that having phase difference $\delta$ of $\pi/2$, is so superposed that the total phase difference is odd times $\pi/2$, whereby cos $\delta$ is substantially zeroed so that the total retardation can be easily precisely measured and the retardation of the sample is precisely obtained.

In a preferred mode of the present invention, a constant value D of 0 <D<1 is so set that a sheet of known retardation is employed when $$|\cos \delta| > D$$

While it is assumed that neither the polarizing plates nor the sample has absorption of light in the above description, the maximum value of not incident light intensity but transmitted light intensity is preferably employed as Io appearing in the equation (3) since there is light absorption in practice.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1A illustrates a relation between optical principal axes of a sample and polarizing direction of polarizing plates;

FIG. 1B illustrates phase difference between ordinary and extraordinary rays transmitted through the sample;

FIG. 2 illustrates distribution of intensity of a detection output from a photodetector with respect to an angle of rotation of polarizing plates;

DESCRIPTION OF THE PREFERRED EMBODIMENTS

Figure 3:
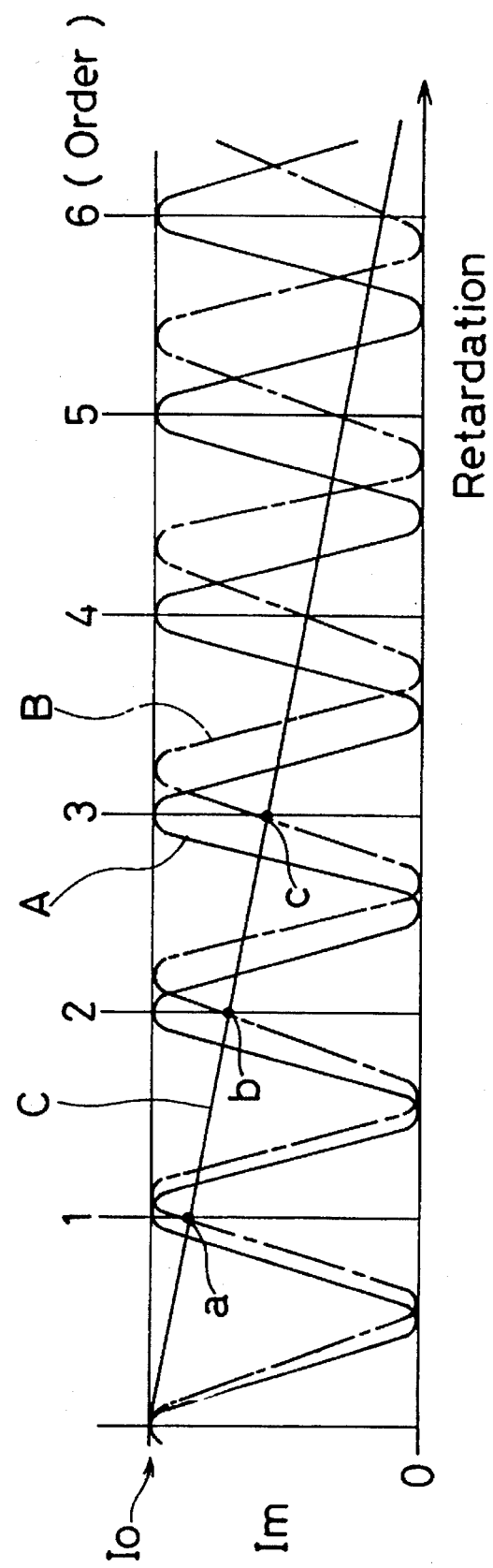
FIG. 3 illustrates an operation of deriving an order according to the present invention.
Figure 4:
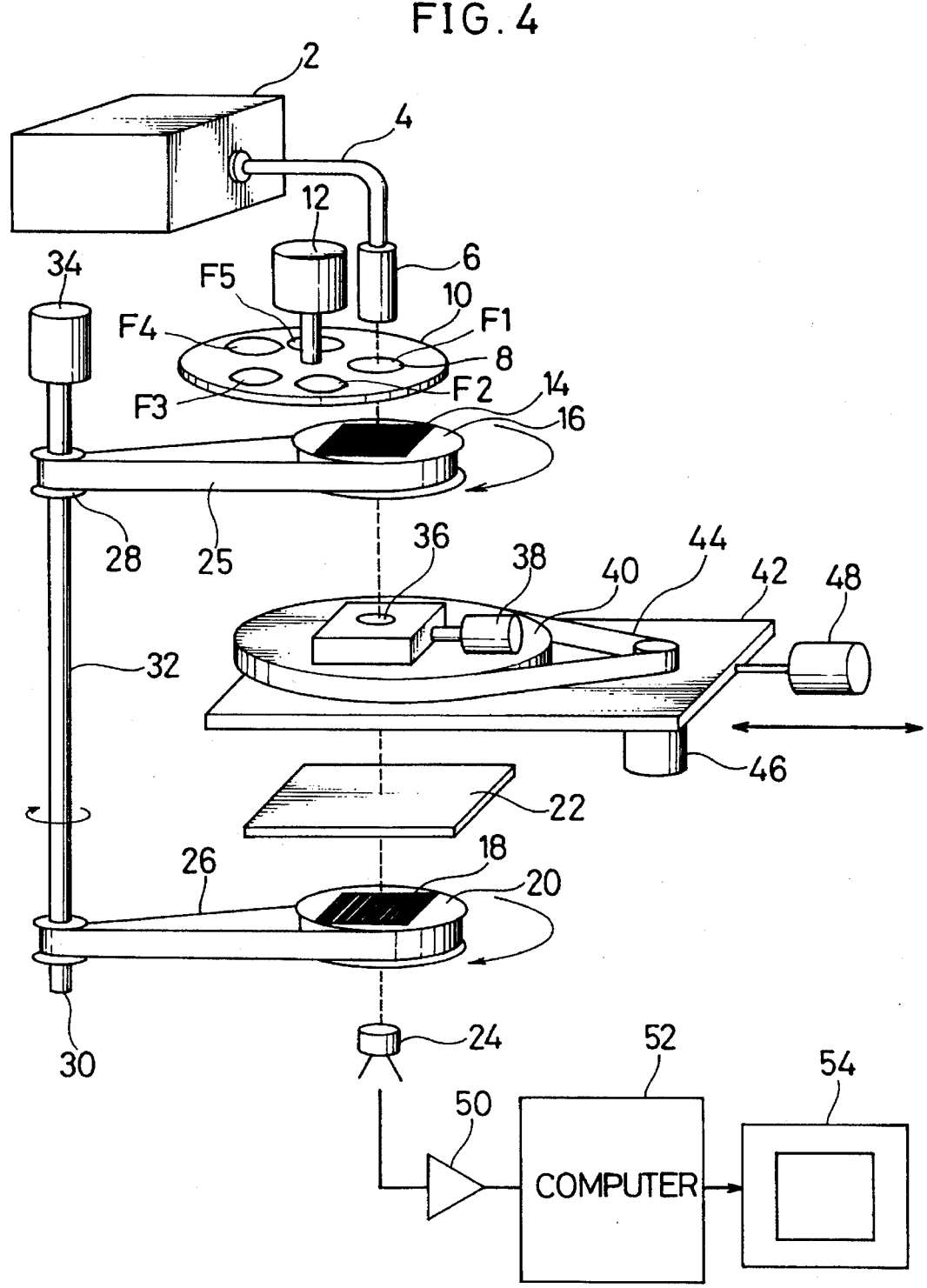
FIG. 4 is a perspective view schematically showing a first embodiment of the present invention.

FIG. 4 shows an apparatus according to a first embodiment of the present invention. A measuring beam which is emitted from a white light source 2 is guided by an optical fiber member 4 to form a parallel beam through a condenser lens 6. A filter part 8, a polarizing plate 14 serving as a polarizer, a phase plate 36, a sample 22 and another polarizing plate 18 serving as an analyzer are arranged on an optical path of the measuring beam between the condenser lens 6 and a photodetector 2 4 successively from the condenser lens 6 side. The filter part 8 is provided with five filters F1 to F5 having different light transmission characteristics along a circumferential direction of a filter holding plate 10. A stepping motor 12 for rotating the filter holding plate 10 selects one of the filters F1 to F5 and inserts the selected one on the optical path of the measuring beam. Among the filters F1 to F5, the filter F1 is a bandpass filter which passes a beam having a wavelength for measuring retardation, while the filters F2 to F5 are those selected to be increased in transmission wavelength difference with respect to the filter F1 successively from F2 to F5.

The polarizing plates 14 and 18 are so arranged that polarizing directions are parallel to each other, and held by holding discs 16 and 20 respectively. The holding discs 16 and 20 are coupled with pulleys 28 and 30 which are fixed onto a shaft 32 through belts 25 and 26 respectively, so that the polarizing plates 14 and 18 are integrally rotated when the shaft 32 is rotated by a stepping motor 34. A mark of a reflector is provided on a portion of a side surface of the holding disc 16 holding the polarizing plate 14, so that a photoelectric detector detects this reflector thereby detecting initial positions of rotation of the polarizing plates 14 and 18.

A measuring beam of a wavelength selected by any of the filters F1 to F5 is transmitted through the polarizing plate 14 to enter the sample 22 which is arranged between the polarizing plates 14 and 18. The measuring beam thus transmitted through the sample 22 enters the photodetector 24 through the polarizing plate 18, to be measured there.

A phase plate 36 is arranged between the polarizing plate 14 and the sample 22 to be insertable and removable by a stepping motor 48. This phase plate 36 is formed by a Babinet-Soleil compensator, so that its own retardation is variable. The retardation of the phase plate 36 is varied by a stepping motor 38. As to the phase plate 36, it is necessary to set its azimuth so that its optical principal axis is parallel or perpendicular to that of the sample 22 . To this end, the phase plate 36 is mounted on a turntable 40, which in turn is rotatably supported by a support 42 so that the phase plate 36 can be rotated by a stepping motor 46 through a belt 44.

An amplifier circuit is provided in order to amplify a detection output of the photodetector 24 while an A/D converter is provided in order to convert the amplified output to a digital signal. Such amplifier circuit and A/D converter are denoted by numeral 50 together. The output thus converted to a digital signal is incorporated in a computer 52 serving both as a data processor and a controller of the measuring apparatus, so that a data-processed result is displayed on a CRT display 54. The computer 52 thus processes the measured data, while transmitting pulses to the respective motors 12, 34, 38, 46 and 48 for controlling rotation thereof.

A method of deciding an order n and measuring retardation by the apparatus shown in FIG. 4 is now described.

In such a state that the phase plate 36 is inserted on the measuring optical path, the filter F1 (transmission wavelength: $\lambda 1$) for selecting a beam having a measurement reference wavelength is located on the measuring optical path. The motor 46 is driven to set the azimuth of the phase plate 36 so that its optical principal axis coincides with that of the sample 22. When the sample 22 is formed by a drawn sheet material, for example, its optical principal axis is coincident with the direction of drawing, whereby the optical principal axis of the phase plate 36 may be matched with the longitudinal direction of the sample 22. In a case of a general sample, having an optical principal axis whose direction is previously unknown, such as a partially fabricated item punched from a sheet material in a prescribed shape, for example, the polarized plates 14 and 18 are first rotated while removing the phase plate 36 from the measuring optical path, to obtain an output of the photodetector 24 with respect to the angles of rotation of the polarizing plates 14 and 18. The computer 52 incorporates the output of the photodetector 24 from a point of time when the reflector provided on the side surface of the holding disc 16 holding the polarizing plate 14 is detected by the photoelectrical detector, to singularly rotate the polarizing plates 14 and 18. The result is as shown in FIG. 2 in polar coordinate display. When difference between outputs at two angle positions separated by 22.5° in front and at the back of the respective angles of rotation of the polarizing plates 14 and 18, i.e., 45° with respect to the respective angles of rotation of the polarizing plates 14 and 18, there are eight angles zeroing the difference (positions of positive-negative inversion) in single rotation of the polarizing plates 14 and 18, and there are four angles maximizing the photodetector output at intermediate positions. The four angle positions are separated by 90° from each other, and the directions are along the optical principal axis of the sample 22 or that perpendicular thereto.

While it is possible to directly obtain the maximum angle position of the photodetector output, it is preferable to obtain the same from the angle positions causing positive-negative inversion of the difference as described above, since change of the photodetector output is so small around the maximum output that the angle position cannot be correctly obtained. However, it is noted that the method of detecting the optical principal axis of the sample 22 is not restricted to this.

After the phase plate 36 is set on the measuring optical path so that its optical principal axis is matched with that of the sample 22, the polarizing plates 14 and 18 are rotated to measure intensity change of the light transmitted through the sample 22 and data as to relation between the angles of rotation of the polarizing plates 14 and 18 and the transmitted light intensity is incorporated. This relation generally exhibits a floral shape such as that shown in FIG. 2.

Then, the polarizing plates 14 and 18 are rotated to such a position that the polarizing direction thereof ds displaced from the optical principal axis of the sample 22 by 45°, and stopped. A trigger is outputted to the A-D converter 50, and retardation of the phase plate 36 is changed so that the value thereof is substantially identical to the maximum value of relation between the previously measured angles of rotation and transmitted light intensity while incorporating 12-bit data, for example. The transmitted light intensity is maximized when the total retardation of the sample 22 and the phase plate 36 is integral times the wavelength of the measuring beam transmitted through the filter F1. This means that the pattern shown in FIG. 2 forms a circle.

The phase plate 36 is brought into this state and the polarizing plates 14 and 18 are returned to measurement starting positions, to again measure a pattern showing relation between the angles of rotation and the transmitted light intensity. If the pattern is not in the form of a complete round (Im/Io=1), the retardation of the phase plate 36 is slightly changed by the motor 38 and the operation is repeated until the pattern reaches a complete round to the utmost. It is assumed that C1 represents cos δ measured at this time.

Then the filter F1 is replaced by the filter F2 (transmission wavelength: λ2), and the polarized plates 14 and 18 are rotated to measure transmitted light intensity. The ratio between maximum and minimum values Io and Im in the currently obtained pattern of FIG. 2. It is assumed that C2 represents cos δ obtained from the ratio Im/Io. A possible order n (even number) is derived from relation between C2, C1 and the equation (5). The filters are successively changed as F3, F4 and F5 to perform similar measurement, whereby four values can be obtained as to the possible order n. Among these, a single order n is decided by a majority operation, for example.

Upon decision of the order n, it is possible to obtain retardation of the sample.

In this measurement, accuracy in a case of zeroing total apparent phase difference of the sample 22 and the phase plate 36 at the reference wavelength by the filter F1 is related to measurement accuracy. Therefore, a half-wavelength plate with respect to a beam having the reference wavelength λ1 is prepared independently of the phase plate 36. After the phase plate 36 is so adjusted that total retardation of the sample 22, the phase plate 36 and the half-wavelength plate is π, i.e., transmitted light intensity is changed between 0 and the maximum upon rotation of the polarizing plates 14 and 18, the half-wavelength plate is removed from the measuring optical path. At this time, total apparent retardation of the sample 22 and the phase plate 36 is 0. According to this method, it is possible to adjust the phase plate 36 in higher sensitivity than that in the case of adjusting the phase plate 36 so that the pattern of transmitted light intensity shown in FIG. 2 forms a circle.

As the order of retardation is increased, interference of ordinary and extraordinary rays is so diffused due to influence by wavelength spreading of as-employed monochrome light that change of the transmitted light intensity upon rotation of the polarizing plates 14 and 18 is reduced and the retardation is apparently reduced. Thus, the as-employed light source preferably has high monochromaticity. As to the light source, it is more preferable to employ a discharge tube to select some emission lines by filters than to select a beam from a continuous spectrum source by a filter. When emission lines of 450.1 nm, 462.4 nm and 467.1 nm of a xenon discharge tube are used so that the emission line of 467.1 nm is employed with a reference wavelength of the emission line of 462.4 nm, for example, $n_o$ appearing in the equation (7) is about 100 so that measurement is enabled up to an order of about 50.

While the phase plate 36 is formed by a Babinet-Soleil compensator which is high-priced, a plurality of plates having known retardation values which are different little by little from each other may be exchangeably provided in place of the phase plate 36 for deciding the order, in a turret system similarly to the filter F1 to F5.

In the relation (FIG. 2) between the angles of rotation of the polarizing plates and the detection output of the photodetector, detection accuracy is reduced when the difference between the maximum and minimum values Io and Im is small. Therefore, it is possible to improve detection sensitivity by determining whether or not the absolute value of cos δ is greater than the constant value D (0<D<1) and automatically inserting the phase plate 36 on the measuring optical path when the determination is of yes.

Figure 5:
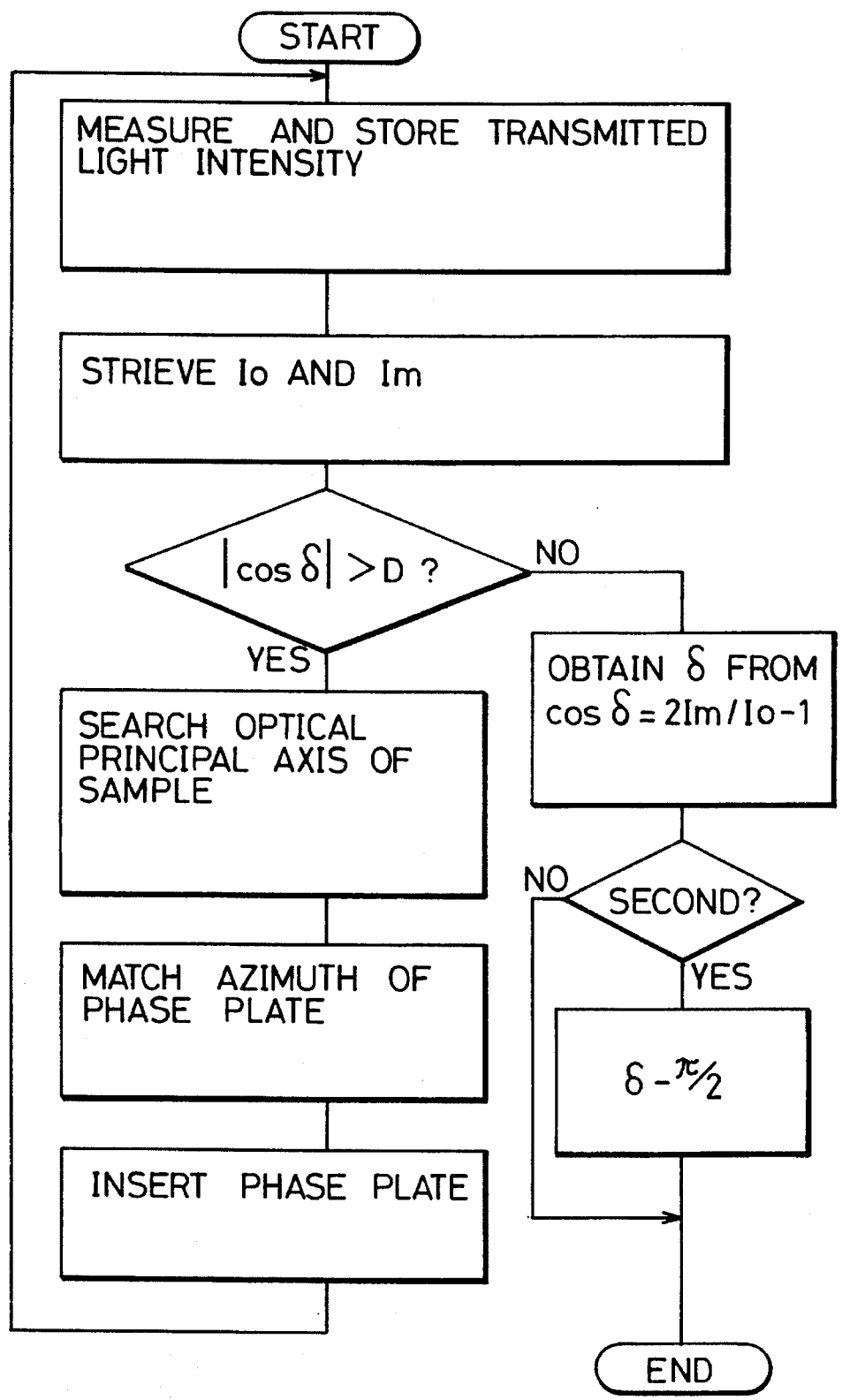
FIG. 5 is a flow chart showing an exemplary operation of the embodiment shown in FIG. 4.

An operation for improving the detection sensitivity in the embodiment shown in FIG. 4 is now described with reference to a flow chart shown in FIG. 5.

The phase plate 36 is set to act as a quarter-wavelength plate with respect to a measuring wavelength.

The phase plate 36 is in a state being removed from the measuring optical path at first. The sample 22 is set in the apparatus, to start the measuring operation. The computer 52 rotates the polarizing plates 14 and 18 for measuring transmitted light intensity every angle of 1°, and stores the measured values in a memory with the data of the angles of rotation of the polarizing plates 14 and 18. Then, the maximum and minimum values Io and Im of the transmitted light intensity are retrieved from the incorporated data. The relation between the transmitted light intensity and the angles of rotation of the polarizing plates 14 and 18 exhibits a floral shape as shown in FIG. 2 on polar coordinates, while this floral shape approximates to a circle when the phase difference δ is around 2π to reduce the difference between the maximum and minimum values, and retardation cannot be correctly obtained. Therefore, a determination is made as to whether or not the absolute value of cos δ is greater than the previously set constant D.

When the absolute value of cos δ is less than D, the phase difference δ is calculated by the equation (3) from the as-obtained Im and Io, to terminate the operation.

When the absolute value of cos δ is greater than D, on the other hand, the direction of the optical principal axis of the sample 22 is searched at first. To this end, values of difference between intensity values of a pair of transmitted beams at angle positions of the polarizing plates 14 and 18 separated from each other by 45° are successively obtained from the data obtained by singularly rotating the polarizing plates 14 and 18 as described above, to obtain the azimuth of the optical principal axis of the sample 22 as an intermediate direction of angle positions separated from each other by 45° in sign inversion of the difference, for example. When this azimuth is obtained, the motor 46 is driven to match the azimuth of the phase plate 36 with the optical principal axis of the sample 22, and the motor 48 is driven to move the phase plate 36 into the measuring optical path. Thereafter the polarizing plates 14 and 18 are rotated to perform measurement.

Since the phase plate 36 is inserted on the measuring optical path, the absolute value of cos δ is reduced below D and retardation in the case of superposing the phase plate 36 is obtained.

At a next step, a determination is made as to whether or not this measurement is after insertion of the phase plate 36 on the measuring optical path (second measurement), and if the determination is of yes, π/2 is subtracted from the as-obtained δ since the phase plate 36 is employed, and retardation of the sample 22 is calculated from this value to terminate the measuring operation.

According to this operation, the situation is automatically determined even if it is difficult to correctly decide the retardation of the sample 22 which is close to $n\lambda/2$, so that the phase plate 36 is automatically inserted on the measuring optical path for performing measurement, whereby no specific determination is required for an operator and the retardation can be easily correctly measured in any case.

When this measuring operation for improving detection sensitivity is performed, the phase plate 36 may be formed by a sheet of known retardation or a quarter-wavelength plate, in place of a Babinet-Soleil compensator.

Figure 6:
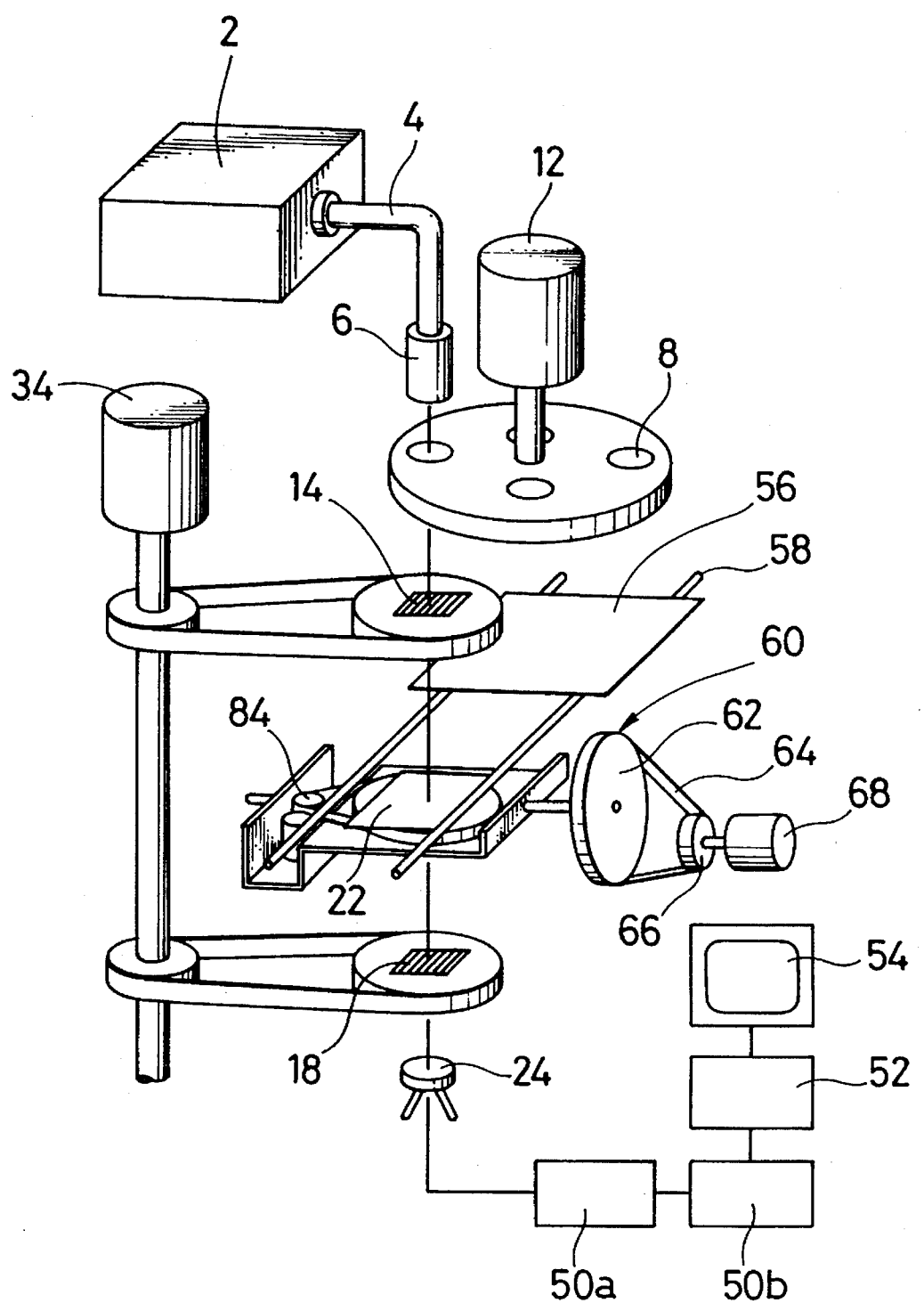
FIG. 6 is a perspective view schematically showing a second embodiment of the present invention.

FIG. 6 shows another embodiment of the present invention, which can measure refractive indices of beams transmitted through a sample at various angles while enabling correct measurement of retardation.

Referring to FIG. 6, a sample 22 is rendered rotatable in its plane and is held by a sample holder 60 so that the sample 22 can be inclined about a straight line along its surface for measurement of refractive indices in three axial directions thereof. A quarter-wavelength plate 56 is held between a polarizing plate 14 and the sample 22 to be insertable on and removable from a measuring optical path along a guide 58.

Figure 7:
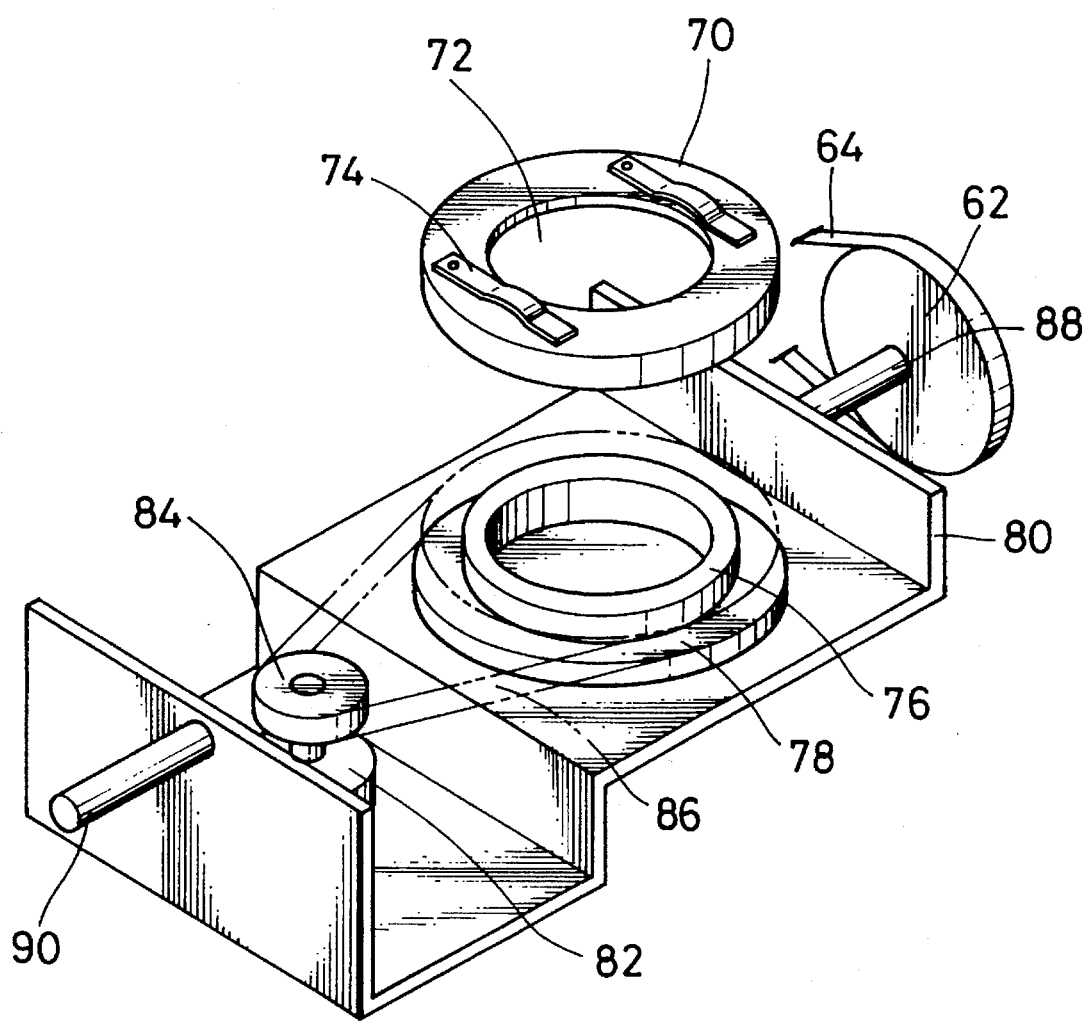
FIG. 7 is an exploded perspective view showing a sample holder in the embodiment shown in FIG. 6.

FIG. 7 illustrates the sample holder 60 in detail. A sample support 70 is provided with a hole 72 in its center and its back surface is hollowed in the form of a ring to define a cavity, while its upper surface is provided with presser plates 74 for pressing and holding the sample 22 in two positions. A turntable 78 having a ring-shaped convex portion 76 to be engaged with the cavity at the back surface of the sample support 70 is mounted on a substrate 80, to rotatably hold the sample support 70 about an axis which is perpendicular to the sample plane. A belt 86 is mounted between a side surface of the sample support 70 which is engaged in the turntable 78 and a pulley 84 which is mounted on a rotary shaft of a stepping motor 82, so that the sample support 70 is rotated by the motor 82. This motor 82 is also mounted on the substrate 80, and mounting surfaces of the motor 82 and the turntable 78 are so formed that the pulley 84 and the sample support 70 are arranged in the same plane. Shafts 88 and 90 are so mounted on a pair of side surfaces of the substrate 80 that central axes of these shafts 88 and 90 are on the surface of the sample support 70. These shafts 88 and 90 are supported on the body of the apparatus shown in FIG. 6. A pulley 62 is mounted on the shaft 88 and a belt 64 is extended across this pulley 62 and a pulley 66 of a stepping motor 68 provided on the body of the apparatus so that the substrate 80 is inclined by the motor 68.

A computer 52 also controls operations of the motors 68 and 82.

The apparatus according to the embodiment shown in FIG. 6 is adapted to measure birefringence of the sample 22 in the following manner:

The sample 22 is mounted on the sample support 70 and a motor 34 is started in such a state that the quarter-wavelength plate 56 is removed from the measuring optical path, to rotate the polarizing plates 14 and 18. The computer 52 calculates retardation R of the sample 22 from the maximum and minimum values Io and Im in FIG. 2, and stores the retardation.

Upon completion of single measurement, the motor 82 is driven to rotate the sample support 70 by a constant angle of 10°, for example, and an operation identical to the above is again performed. Thus, retardation is obtained while changing the direction of the sample 22.

Further, the aforementioned measuring operation is repeated while changing the angle of inclination of the sample 22 by driving the motor 68 for inclining the sample support 70 by a constant angle of 5°, for example, to obtain retardation.

The computer 52 reads the angles of rotation and inclination of the sample support 70 by driving pulses for the motors 82 and 68 respectively.

When difference between maximum and minimum values of an output from a photodetector 24 is so small that it is determined difficult to precisely obtain retardation in this measuring operation, the quarter-wavelength plate 56 is moved onto the measuring optical path to perform the same measurement again. The computer 52 controls the determination as to whether or not the quarter-wavelength plate 56 is moved onto the measuring optical path and an operation for moving the quarter-wavelength plate 56, as shown in FIG. 5.

According to the embodiment shown in FIG. 6, birefringence of a sheet-type sample can be measured while automatically adjusting angles of inclination and rotation of the sample and automatically inserting and removing the quarter-wavelength plate 56, whereby it is possible to automatically measure refractive indices in three axial directions in high accuracy.

Figure 8:
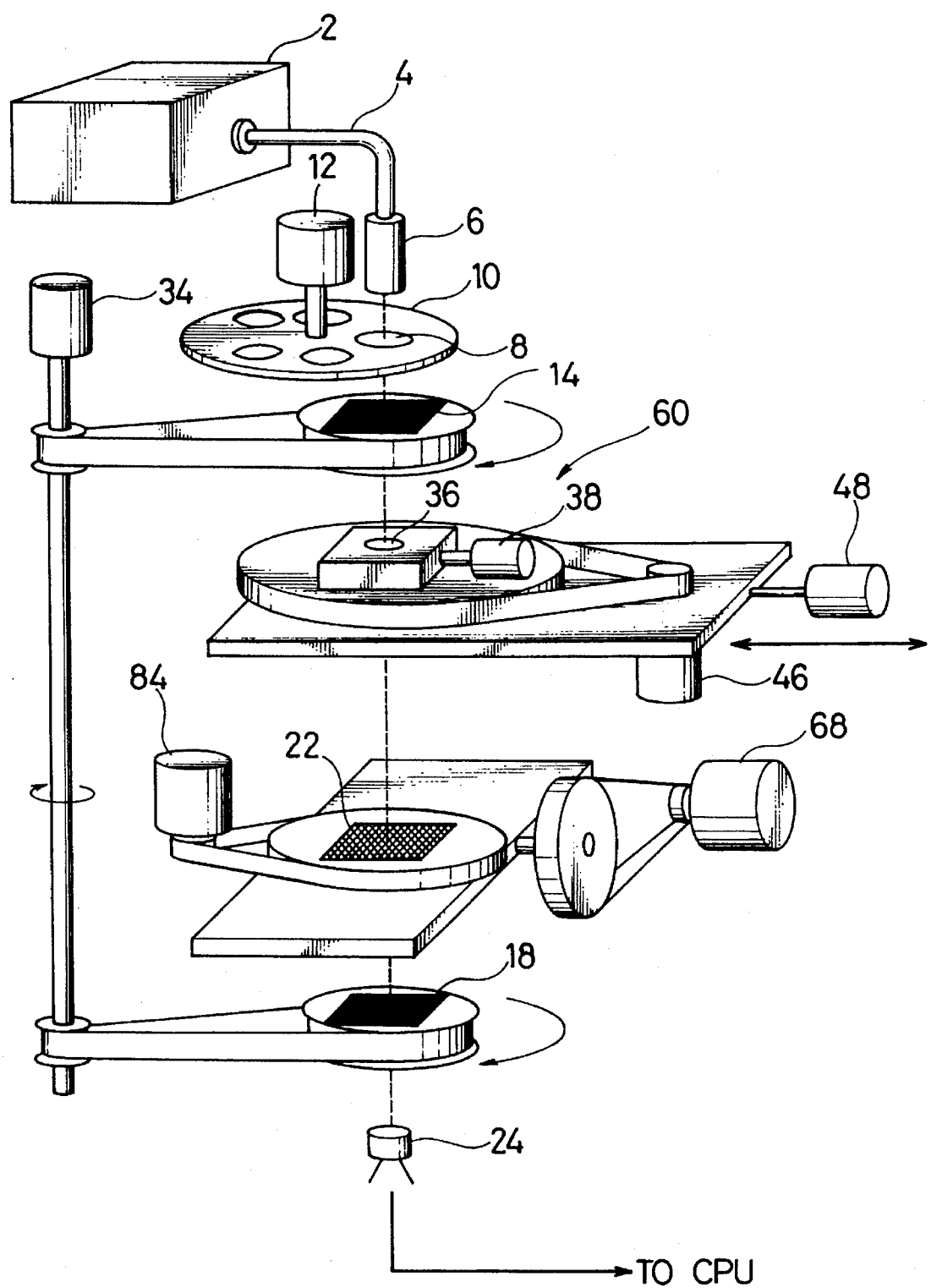
FIG. 8 is a perspective view schematically showing a third embodiment of the present invention.

FIG. 8 shows such an embodiment that the sample holder 60 employed in the apparatus shown in FIG. 6 is combined with the measuring apparatus shown in FIG. 4.

In the embodiment shown in FIG. 8, a phase plate 36 is formed by a Babinet-Soleil compensator. This phase plate 36 is adapted to decide an order of retardation using a plurality of wavelengths, while the phase plate 36 can also serve as a phase plate for moving retardation of a sample by a quarter wavelength when difference between maximum and minimum values Io and Im of a photodetector output is small. A sample holder 60 can rotate and incline the sample 22. Consequently, it is possible to correctly obtain the order and retardation according to the measuring apparatus shown in FIG. 8, while it is also possible to measure refractive indices in three axial directions in high accuracy while changing angles of rotation and inclination of the sample 22.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method of measuring birefringence comprising the steps of:

superposing a phase plate on a sample so that a phase difference of the total retardation of said sample and said phase plate is integral times $2\pi$ with respect to a measuring beam of a first wavelength, employing a measuring beam of a second wavelength being approximate to said first wavelength in this state, measuring the currently transmitted light intensity in the course of relatively singularly rotating said two polarizing plates such that said polarizing plates maintain their polarizing directions in a constant relation with respect to said sample being arranged therebetween, applying the ratio between a maximum value Io and a minimum value Im of the currently transmitted light intensity to a previously prepared relation between the order of retardation and said ratio for deriving the order of retardation of said sample, calculating said retardation based on said derived order.

2. A method of measuring birefringence in accordance with claim 1, wherein said two polarizing plates are set in parallel nicol relation to each other, and said order is derived from the relation between Im/Io and the order of retardation.

3. A method of measuring birefringence in accordance with claim 1, wherein
said two polarizing plates are set in parallel nicol relation to each other, and said order is derived from the relation between (Io–Im)/Io and the order of retardation.

4. A method of measuring birefringence in accordance with claim 2, wherein
a possible said order n is derived from the following relation, assuming that C1 represents cos δ of phase difference δ obtained when said phase plate is so superposed on said sample that said phase difference of the total retardation of said sample and said phase plate is integral times $2\pi$ with respect to said measuring beam of said first wavelength $\lambda 1$ and C2 represents cos δ obtained from Im/Io in the course of relatively singularly rotating said two polarizing plates in place of said second measuring beam of said wavelength $\lambda 2$ in this state:

$$C2 = C1 \cdot \sin\{\pi/2 - (n/2)(\lambda_2 - \lambda_1) 2\pi/\lambda_2\}.$$

5. A method of measuring birefringence in accordance with claim 1, wherein
a graph showing the relation among said maximum value Io and minimum value Im of said transmitted light intensity and said order n is previously obtained using said first and second measuring beams and the ratio between Io and Im with said second measuring beam is applied to said graph for deriving said order n on said graph.

6. A method of measuring birefringence in accordance with claim 1, wherein
a plurality of values are obtained as to a possible said order while successively changing measuring wavelengths, for deriving the most probable said order n.

7. A method of measuring birefringence in accordance with claim 1, wherein
a half-wavelength plate with respect to said measuring beam of said first wavelength is prepared independently of said phase plate when said phase plate is superposed on said sample so that said phase difference of the total retardation of said sample and said phase plate is integral times $2\pi$ with respect to said measuring beam of said first wavelength, and said half-wavelength plate is removed from a measuring optical path after said phase plate is so adjusted that the total retardation of said sample, said phase plate and said half-wavelength plate is integral times $\pi$.

8. A method of measuring birefringence in accordance with claim 1, wherein
a quarter-wavelength plate is arranged on a measuring optical path when the ratio or difference between said maximum value Io and minimum value Im of said transmitted light intensity obtained when said two polarizing plates are relatively rotated with respect to said sample is not within a predetermined reference range and thereafter said two polarizing plates are relatively rotated with said sample for calculating said retardation on the basis of said maximum value Io and minimum value Im of current said transmitted light intensity.

9. An apparatus for measuring birefringence, comprising:
a light source part for supplying a measuring beam to a measuring optical path;
a filter part for selecting a wavelength of said measuring beam;
a polarizing and analyzing part having two polarizing plates being arranged on said measuring optical path and maintaining polarizing directions in a constant relation, said two polarizing plates being relatively rotated with respect to a sample being arranged therebetween;
a phase plate of variable retardation being arranged on a position of said measuring optical path between one of said polarizing plates and said sample;
a moving mechanism for moving said phase plate between said position on said measuring optical path and a position out of said measuring optical path;
a rotating mechanism for rotating said phase plate about said measuring optical path for matching the direction of an optical principal axis of said phase plate with that of said sample;
a photodetecting part for detecting said measuring beam being transmitted through said polarizing and analyzing part, said phase plate and said sample; and
a data processing and control part for controlling said selection of said filter in said filter part, said rotation of said polarizing and analyzing part, retardation change of said phase plate and operations of said moving and rotating mechanisms as well as calculating retardation of said sample by incorporating an output signal from said photodetecting part.

10. An apparatus for measuring birefringence in accordance with claim 9, wherein
said data processing and control part selects a measuring beam of a first wavelength by said filter part, drives said moving mechanism to arrange said phase plate on said measuring optical path, drives said rotating mechanism to match the direction of said optical principal axis of said phase plate with that of said sample, changes retardation of said phase plate so that the phase difference of the total retardation of said sample and said phase plate is integral times $2\pi$ with respect to said measuring beam of said first wavelength, thereafter selects a measuring beam of a second wavelength being approximate to said first wavelength by said filter part, relatively singularly rotates said polarizing and analyzing part with respect to said sample, applies the ratio between maximum value Io and minimum value Im of currently transmitted light intensity to a previously prepared relation between the order of retardation and said ratio for deriving the order n of retardation of said sample, and thereafter calculates said retardation based on said derived order.

11. An apparatus for measuring birefringence in accordance with claim 9, wherein
said data processing and control part comprises detecting means for detecting whether or not the ratio or the difference between a maximum value Io and a minimum value Im of said output signal from said photodetecting part generated when said polarizing and analyzing part is relatively singularly rotated with respect to said sample in a state removing said phase plate from said measuring optical path is within a predetermined reference range, calculates retardation on the basis of said maximum value Io and minimum value Im when said ratio or difference between said maximum value Io and minimum value Im of said output signal from said photodetecting part is within said reference range, drives said moving mechanism to arrange said phase plate on said measuring optical path when said ratio or difference between said maximum value Io and minimum value Im of said output signal from said photodetecting part is not within said reference range, drives said rotating mechanism to match the direction of said optical principal axis of said phase plate with that of said sample, changes retardation of said phase plate so that the said phase plate serves as a quarter-wavelength plate with respect to said measuring beam of said first wavelength, thereafter relatively singularly rotates said polarizing and analyzing part with respect to said sample, and calculates retardation on the basis of said maximum value Io and minimum value Im of current said output signal from said photodetecting part.

12. An apparatus for measuring birefringence in accordance with claim 9, further comprising a mechanism for rotating said sample in its plane and a mechanism for inclining said sample about a straight line along the surface of said sample, wherein said data processing and control part calculates said retardation while rotating and inclining said sample by constant angles.

13. An apparatus for measuring birefringence in accordance with claim 10, wherein a half-wavelength plate with respect to said measuring beam of said first wavelength is further provided to be insertable on and removable from said measuring optical path, and said data processing and control part so adjusts said phase plate that the total retardation of said sample, said phase plate and said half-wavelength plate is integral times $\pi$ when said retardation of said phase plate is changed so that said phase difference of the total retardation of said sample and said phase plate is integral times $2\pi$ with respect to said measuring beam of said first wavelength and thereafter removes said half-wavelength plate from said measuring optical path.

14. An apparatus for measuring birefringence, comprising:

a light source part for supplying a measuring beam to a measuring optical path;

a filter part selecting a wavelength of said measuring beam;

a polarizing and analyzing part having two polarizing plates being arranged on said measuring optical path and maintaining polarizing directions in a constant relation, said two polarizing plates being relatively rotated with respect to a sample being arranged therebetween;

a quarter-wavelength plate being arranged to be insertable on and removable from a position of said measuring optical path between one of said polarizing plates and said sample;

a moving mechanism for moving said quarter-wavelength plate between said position on said measuring optical path and a position out of said measuring optical path;

a rotating mechanism for rotating said quarter-wavelength plate about said measuring optical path to match the direction of an optical principal axis of said quarter-wavelength plate with that of said sample;

a photodetecting part for detecting said measuring beam being transmitted through said polarizing and analyzing part, said quarter-wavelength plate and said sample; and a data processing and control part controlling said selection of said filter in said filter part, said rotation of said polarizing and analyzing part, retardation change of said quarter-wavelength plate and operations of said moving and rotating mechanisms and being provided with detecting means for detecting whether or not the ratio or the difference between a maximum value Io and a minimum value Im of an output signal generated from said photodetecting part when said polarizing and analyzing part is relatively singularly rotated with respect to said sample is within a predetermined reference range, for calculating retardation on the basis of said maximum value Io and said minimum value Im when said ratio or said difference between said maximum value Io and said minimum value Im of said output signal from said photodetecting part is within said reference range while driving said moving mechanism for arranging said quarter-wavelength plate on said measuring optical path and driving said rotating mechanism for matching said direction of said optical principal axis of said quarter-wavelength plate with that of said sample when said ratio or said difference between said maximum value Io and said minimum value Im of said output signal from said photodetecting part is not within said reference range, and thereafter calculating said retardation on the basis of said maximum value Io and said minimum value Im of said output signal generated from said photodetecting part when said polarizing and analyzing part is relatively singularly rotated with respect to said sample.

15. An apparatus for measuring birefringence in accordance with claim 14, further comprising a mechanism for rotating said sample in its plane and a mechanism for inclining said sample about a straight line along the surface of said sample, wherein said data processing and control part calculates said retardation while rotating and inclining said sample by constant angles.

* * * * *